United States Patent [19]

Kobayashi et al.

[11] 4,389,125
[45] Jun. 21, 1983

[54] METHOD FOR MEASURING SURFACE TEMPERATURE DISTRIBUTION AND SYSTEM

[75] Inventors: Ikuro Kobayashi, Machida; Kyozo Shimizu, Tokyo, both of Japan

[73] Assignee: VLSI Technology Research Association, Tokyo, Japan

[21] Appl. No.: 189,635

[22] Filed: Sep. 22, 1980

[51] Int. Cl.³ .................. G01K 7/01; G01K 25/18; H05B 1/02
[52] U.S. Cl. .................................. 374/164; 219/494
[58] Field of Search .............. 73/355 R, 362 SC; 219/328; 364/481, 557; 374/164

[56] References Cited

U.S. PATENT DOCUMENTS

| | | | |
|---|---|---|---|
| 3,434,332 | 3/1969 | Maley | 73/355 R X |
| 3,463,007 | 8/1969 | Jones et al. | 73/355 R |
| 3,465,150 | 9/1969 | Hugle | 73/355 R |
| 3,766,781 | 10/1973 | Roberts | 73/355 R |
| 3,868,508 | 2/1975 | Lloyd | 250/338 X |
| 3,991,302 | 11/1976 | Danner | 364/481 |
| 4,008,616 | 2/1977 | Murray | 73/355 R |
| 4,123,938 | 11/1978 | Hamilton | 73/362 SC X |
| 4,221,125 | 9/1980 | Oliver et al. | 73/362 SC X |
| 4,228,684 | 10/1980 | Templin | 73/362 SC |

FOREIGN PATENT DOCUMENTS 1443162  7/1976  United Kingdom ........... 73/362 SC

OTHER PUBLICATIONS

Publication, IEEE Transactions-vol. IECI-20, No. 4, Nov. 1973, "Computer Based Thermographic Displays and Techniques", pp. 200-205.

Primary Examiner—Daniel M. Yasich
Attorney, Agent, or Firm—Staas & Halsey

[57] ABSTRACT

A method for easily measuring surface temperature distribution of a sample consisting of a plurality of coexisting materials having different radiation factors at a specified temperature and a system for performing the surface temperature measuring method. In this measuring method, a sample is at first kept at a known temperature, and the amount of infrared rays radiated from a plurality of narrow regions divided on the surface of the sample is obtained. This measurement is performed at least twice at two known temperatures and therefrom temperature coefficients of infrared rays of each of a plurality of subdivided regions on the surface of the sample are then obtained. Succeedingly, with a sample being under the measuring condition, the amount of infrared rays radiated from a plurality of regions on the surface of the sample is measured. On the basis of such amounts of infrared rays and the temperature coefficients, respective unknown temperatures of the plurality of regions subdivided on the surface of the sample can be determined.

20 Claims, 3 Drawing Figures

METHOD FOR MEASURING SURFACE TEMPERATURE DISTRIBUTION AND SYSTEM

BACKGROUND OF THE INVENTION

1. Field of the Invention

This invention relates to a method for measuring temperature distribution on the surface of a sample and a system for the same. Moreover, this invention relates to a method for easily measuring temperature distribution on the surface of a sample consisting of a plurality of coexisting materials having different radiation coefficients of infrared ray at the specified temperature and a system for the same.

2. Description of the Prior Art

Conventionally, for the measurement of surface temperature of a material, an amount of the radiated ray, such as infrared ray, is measured in order to know an intensity of heat radiated from the surface of said material, and it is calibrated by temperature. Since an amount of radiated ray at the specified temperature is different according to a material, temperature calibration mentioned above is required. Therefore, in order to calibrate the amount of radiated ray to a temperature, it is necessary to know the radiation coefficient of the radiated ray of the sample to be measured.

In other words, first of all, it is necessary to previously search an intensity of radiated heat at each temperature of a material having the radiation coefficient of 1.0, for example, a black radiation body. Then, an intensity of radiated heat of the sample to be measured is converted to a value of a sample having the radiation coefficient of 1.0. For example, a radiation coefficient of a sample is considered as $\alpha$, and the above conversion can be done on the basis of the equation, radiated heat intensity x $1/\alpha$. Then, an actual temperature of the sample can be determined from the relation between a radiated heat intensity and each temperature of the material having a radiation coefficient of 1.0 searched previously.

The method mentioned above easily provides a surface temperature distribution of a sample consisting of a homogeneous material having the previously known radiation coefficient.

However, in the case of a sample consisting of various coexisting materials such as the surface of an integrated circuit, if the radiation coefficient of each region at the surface of said sample is unknown, a surface temperature distribution cannot be obtained. This is a serious disadvantage of the conventional method. Moreover, it is very difficult to know the radiation co-efficient of each region on the surface of the abovementioned sample.

SUMMARY OF THE INVENTION

It is an object of this invention to offer a method for easily measuring temperature distribution of the sample surface and a system for the same.

It is another object of this invention to offer a method for measuring temperature distribution of the sample surface without knowing the radiation coefficients of the radiated heats and a system for the same.

It is an additional object of this invention to offer a method for measuring temperature distribution of the sample surface without knowing the radiation coefficients of the radiated rays and a system for the same.

It is a further object of this invention to offer a method for easily measuring temperature distribution of the sample surface consisting of a plurality of co-existing materials having different radiation coefficients of the radiated rays and a system for the same.

It is still a further object of this invention to offer a method for easily measuring temperature distribution of the surface of a semiconductor integrated circuit and a system for the same.

The surface temperature distribution measuring method of this invention is characterized by: a sample to be measured is kept at a known temperature, the amount of rays radiated respectively from a plurality of subdivided narrower regions of the sample surface is obtained at least at two known temperatures, temperature coefficients of the amount of radiated rays in the respective regions of said surface are obtained, and unknown temperatures of said respective regions are obtained from the amount of rays radiated respectively from said regions of said sample being placed under the measuring condition and said temperature coefficients.

DESCRIPTION OF THE PREFERRED EMBODIMENT

Figure 1:
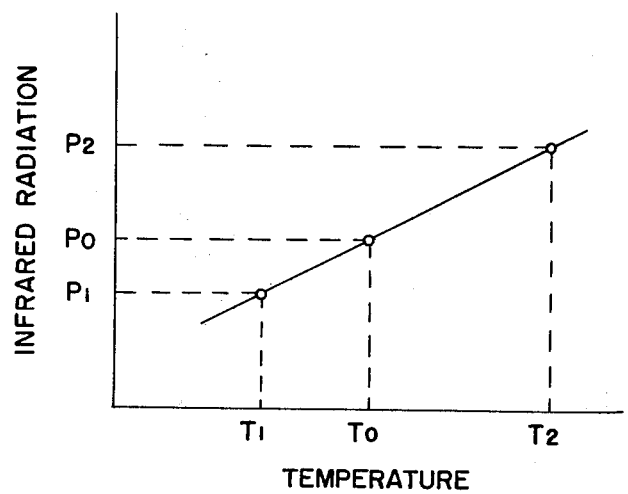
FIG. 1 shows a graph indicating a relation between the amount of radiated infrared ray and temperature in order to explain the basic idea of this invention.

FIG. 1 shows graphs indicating the relation between the amount of radiated infrared ray and temperature for explaining the basic idea of this invention. In this invention, the amount of ray, particularly the amount of infrared ray radiated from the surface is detected in order to obtain a radiated heat intensity of the surface of the sample. Thus, the following explanation is made on the basis of the amount of the infrared ray instead of a radiated heat intensity.

According to the basic idea of this invention, a sample is at first kept at the first known temperature $T_1$ and an amount of the infrared ray $P_1$ radiated from the surface is obtained. Next, the sample is set to the second known temperature $T_2$ and the amount of the infrared ray $P_2$ radiated from the surface is obtained. Then, a ratio between the difference $(P_2-P_1)$ of the two amounts of the infrared rays and the difference $(T_2-T_1)$ of the known temperatures is calculated, and thereby the rate of infrared ray to temperature, namely the temperature coefficient can be obtained. Then, the sample is set to the measuring condition and the amount of infrared ray $P_0$ radiated from the sample surface is obtained. The desired unknown temperature $T_0$ is obtained, for example, from the following equation by making use of the previously obtained temperature coefficient of the infrared ray.

$$(P_2-P_1)/(T_2-T_1)=(P_0-P_1)/(T_0-T_1) \quad T_0=(T_2-T_1)/(P_2-P_1)\cdot(P_0-P_1)+T_1 \quad (a)$$

As explained above, the basic idea of this invention utilizes the proposition that the amount of infrared ray and temperature are approximately proportional. Strictly speaking, the amount of infrared ray and temperature are not proportional, but they can approximately be put into the proportional relation by using a linearizer.

As will be understood from the above explanation, the surface temperature of the sample can be detected according to this invention without relation of a radiation coefficient of the infrared rays of materials forming the sample. In addition, required for obtaining temperature distribution is only detection of the amount of infrared ray for the subdivided plurality of regions on the surface of the sample. Moreover, since temperature range of unknown temperature can be forecasted to a certain degree, it is desirable to set the first and second known temperatures $T_1$ and $T_2$ to the lower and upper ends of such temperature range.

A more accurate temperature coefficient can be obtained by measuring the amount of infrared ray for the other known temperatures than said first and second known temperatures $T_1$, $T_2$ in order to obtain a temperature coefficient of the amount of infrared ray.

Then, an embodiment of a surface temperature distribution measuring system utilizing a measuring method of this invention will be explained hereunder.

Figure 2:
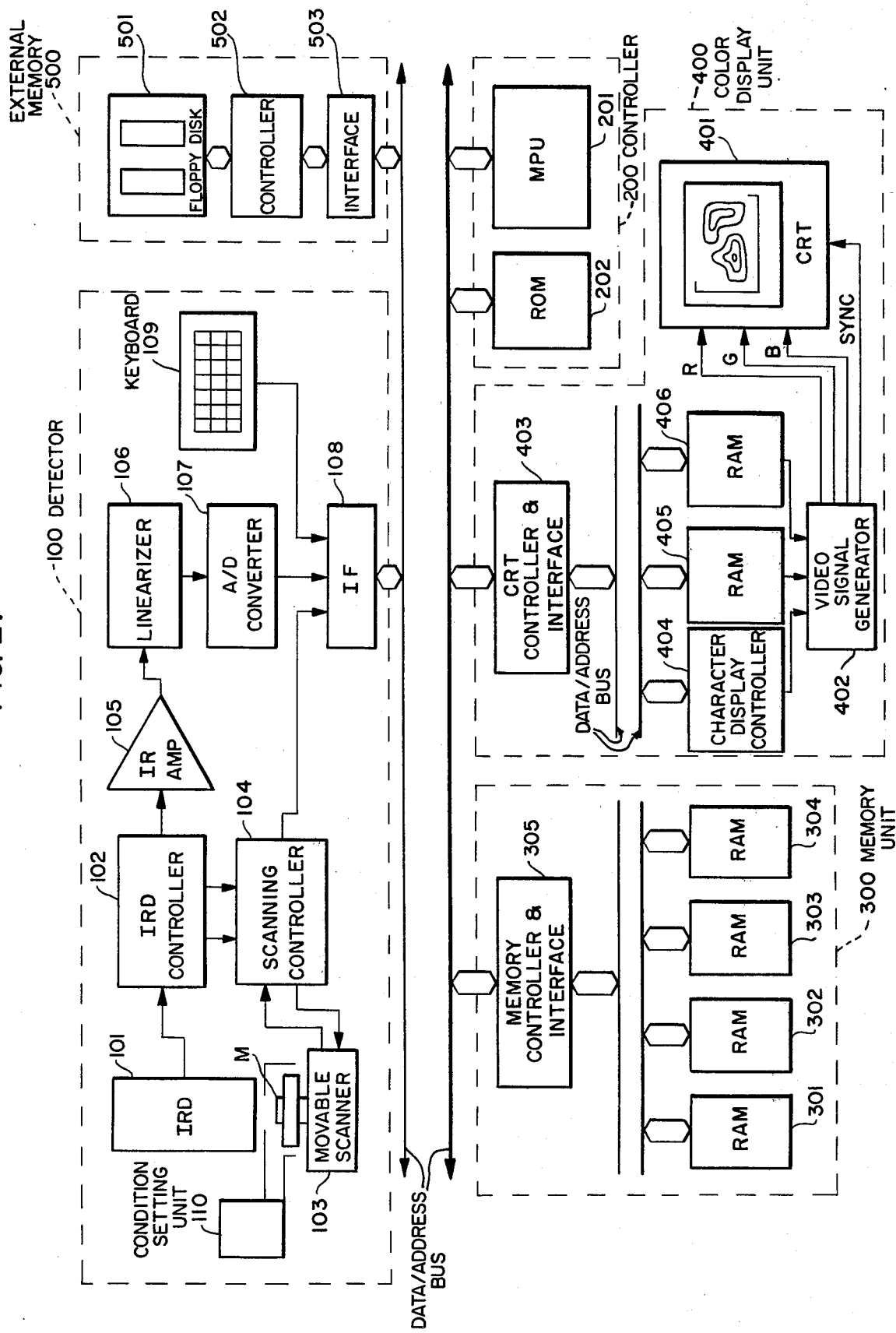
FIG. 2 is a block diagram indicating an embodiment of the measuring system of this invention.

FIG. 2 is the block diagram indicating an organization of the measuring system.

This system comprises a detector 100 which detects an amount of infrared ray, a controller 200 which controls the system as a whole and performs operations for obtaining the temperature coefficient of the infrared ray and unknown temperature of the sample, a memory unit 300 which stores distribution of infrared ray and is used at the time of operations, a display unit 400 which displays distribution of the amount of infrared ray and distribution of unknown temperatures and an external memory unit 500 which stores various kinds of information.

The detector 100 comprises an infrared ray detector 101 for measuring an amount of infrared ray at the surface of the sample M, an infrared ray detector controller 102 which controls the detector, a movable scanner 103 on which the sample M is mounted and a scanning controller 104 which controls the movable scanner. An amount of infrared ray radiated from a plurality of narrowly subdivided regions on the surface of the sample can be measured with these units.

The infrared ray detector 101 is provided, for example, with a light receiving element, which converts an amount of infrared ray into an electrical signal. Such electrical signal is then amplified by an amplifier 105 and input to a linearizer 106.

Strictly speaking, the amount of infrared ray and temperature are not in linear relation and the amount of the infrared ray and the electrical signal are also not always in the linear relation due to characteristic of the light receiving element. Therefore, the linearizer 106 is provided in order to make linear the relation between temperature and an electrical signal representing an amount of the infrared ray.

An electrical signal thus linearized is converted to a digital signal by an A/D converter 107.

Figure 3:
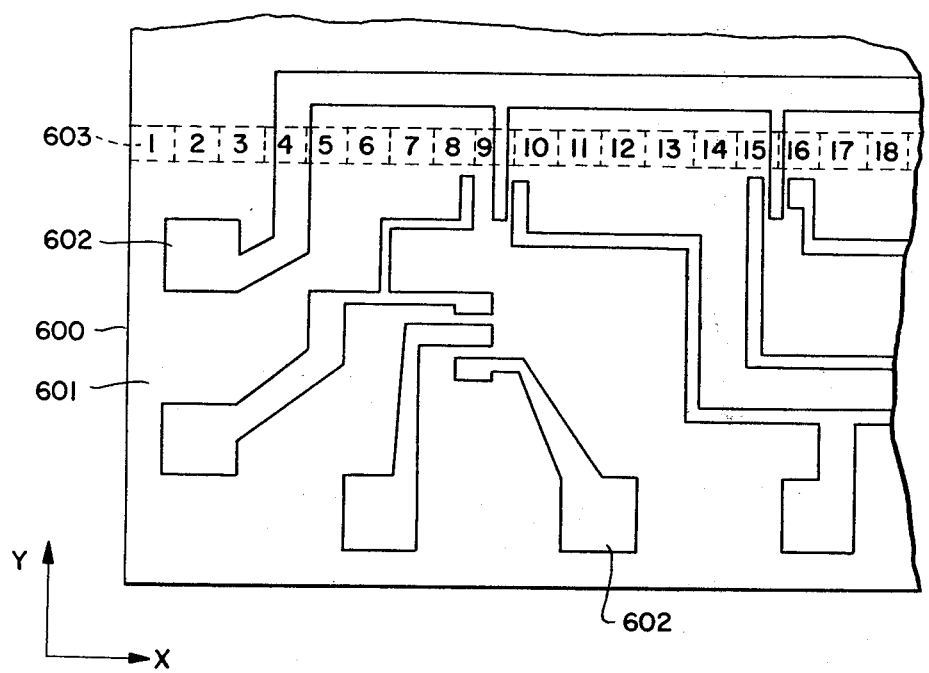
FIG. 3 is a plan view indicating an example of a plurality of regions on the sample surface.

FIG. 3 is a plan view indicating an example of a plurality of regions on the surface of a semiconductor integrated circuit used as the sample. In the case of a semiconductor integrated circuit, patterns are usually formed with various materials on the surface of silicon semiconductor substrate 600. 601 is the surface of $SiO_2$ film and 602 is the aluminum wiring and electrode pattern.

Such a semiconductor integrated circuit is mounted on the movable scanner 103 as the sample and the surface of such sample M is scanned while it moves in the X and Y directions. The scanning is carried out, for example, from the left to right as indicated by the broken line 603, and thereby amounts of infrared rays radiated respectively from the narrowly subdivided regions 1, 2, 3, ..., 18 are detected as the digital signals. Since the semiconductor integrated circuit surface is very narrow, an infrared ray microscope is used for detection of the infrared ray of each region. A digital signal information of each region thus obtained is stored in the memory 300 via an interface 108 (FIG. 2). As shown in FIG. 2, 109 is a keyboard for giving various pieces of information to the detector 100 from the outside. In addition, 110 is a condition setting unit which can put the sample M into the known temperature condition or into the measuring condition and is provided with a heater in order to keep the sample M under the known temperature.

With further reference to FIG. 2, the controller 200 comprises a microprocessor unit 201 and a read-only-memory ROM 202 which stores control programs for arithmetic operations, etc.

The memory 300 comprises four RAMs 301, 302, 303, 304, and a memory controller 305 which controls such RAMs. The RAM 301 is used for arithmetic operations, RAM 302 stores various pieces of information regarding the plurality of regions on the sample surface and amount infrared ray under the known temperature $T_1$, RAM 303 stores the information under the known temperature $T_2$, and RAM 304 stores said information under the measuring condition.

The display unit 400 comprises a cathode ray tube CRT 401 for displaying pictures and a video signal generator 402 which sends the video signals R, G, B, SYNC thereto. The video signals R, G, B are color video signals. 403 is a CRT controller which controls CRT 401, etc. 404 is a controller for displaying characters. 405, 406 are RAMs for temporarily storing display information which is sent from the RAMs 301, 302, 303, and 304 of the memory 300.

The external memory 500 has, for example, a floppy disk 501, controller 502 and interface 503.

The digital signal information of infrared rays corresponding to respective positions of a plurality of regions of the sample surface obtained by the detector 100 is respectively stored in the RAMs 301, 302, 303, and 304. The arithmetic operations for obtaining the unknown temperature distribution are carried out after the region in the RAMs and plurality of regions on the sample surface are mutually aligned so that they correspond on a one-to-one basis. The alignment can be made, for example, by storing a couple of data required for arithmetic operations such as $P_1$ and $P_2$, $P_1$ and $P_0$ in the RAMs 405, 406 and by displaying such data on the CRT 401.

The operations which are carried out according to the abovementioned arithmetic operations will be explained hereunder.

A couple of data regarding known temperatures are shifted to the RAMs 405, 406 from the RAMs 302, 303, and then alignment is performed on the CRT 401. At this time, the RAM 301 is used for correcting an error of alignment. Upon completion of the alignment, the arithmetic operations for obtaining a difference between a couple of infrared rays $P_1$, $P_2$ are performed for each region among the plurality of regions of the sample surface, and the result is stored in the external memory 500. This result is $(P_2-P_1)$ and the temperature coefficient of an infrared ray amount can be obtained easily from the data and $(T_2-T_1)$. Then, the information of a digital signal $P_0$ of an infrared ray amount obtained under the specified measuring condition is shifted to the RAM 304, while the information $P_1$ at the known temperature $T_1$ is shifted to the RAMs 405, 406. Thus, alignment is also performed as explained above. As a result, the information $(P_0-P_1)$ is stored in the external memory 500. Finally, from the information $(P_2-P_1)$, $(P_0-P_1)$, the unknown temperature $T_0$ of respective regions is obtained on the basis of the abovementioned equation (a), and it is stored in the RAM 405. Thereby, a surface temperature distribution diagram is displayed on the CRT 401 in different colors.

For the specified measuring condition means, for example, in the case of a semiconductor integrated circuit, the operating condition is established by applying a current.

A surface temperature distribution of a semiconductor integrated circuit under the operating condition can be used for failure analysis and testing, etc.

In this embodiment, an infrared ray microscope is used in order to obtain the surface temperature distribution of a small sample, such as a semiconductor integrated circuit, etc., but a telescope may also be used for detecting radiated heat or light for the purpose of scanning of the sample in case of obtaining temperature distribution of a large sample consisting of co-existing materials having different radiation coefficients.

As explained previously, according to this invention, surface temperature distribution can be obtained without knowing the radiation coefficients of radiated heats due to the infrared ray, etc. of the sample surface. In addition, according to this invention, temperature distribution of the surface of a sample consisting of a plurality of coexisting materials having different radiation coefficients of radiated heat can easily be measured. Moreover, according to this invention, temperature distribution on the surface of a semiconductor integrated circuit can be easily measured and the result can be effectively used for failure analysis and testing of integrated circuits.

What is claimed is:

1. A method for measuring a surface temperature distribution of a sample, comprising the steps of:
    (a) keeping a sample, comprising a plurality of coexisting materials with different radiation coefficients of radiated rays at the same temperature and divided into a narrowly subdivided plurality of surface regions, at a first known temperature and measuring an amount or rays radiated respectively from each of the narrowly subdivided plurality of regions on the surface of said sample;
    (b) keeping said sample at a second known temperature and measuring an amount of ray radiated respectively from each of said narrowly subdivided plurality of surface regions;
    (c) keeping said sample at an unknown temperature and measuring an amount of ray radiated respectively from each of said narrowly subdivided plurality of surface regions; and
    (d) obtaining the temperatures of respective ones of said narrowly subdivided plurality of surface regions from said amount of radiated rays measured at said first and second known temperatures, and said amount of radiated rays measured at said unknown temperature.

2. A method for measuring surface temperature distribution in accordance with said claim 1, wherein said radiated ray is an infrared ray.

3. A method for measuring surface temperature distribution in accordance with said claim 1 or 2, wherein said sample is an integrated circuit element.

4. A method for measuring surface temperature distribution in accordance with said claim 3, wherein said unknown temperature is an operating temperature obtained by applying a current to said integrated circuit element.

5. A method for measuring surface temperature distribution in accordance with said claim 1 further comprising the steps of:
    keeping said sample at a third known temperature other than said first and second known temperatures and measuring the amount of radiated ray of each of said narrowly subdivided plurality of regions; and obtaining the temperature coefficients of said radiated rays from amounts of radiated rays under said first, second and third known temperatures.

6. A system for measuring surface temperature distribution of a sample having a surface comprising a plurality of coexisting materials with different radiation coefficients of radiated rays and divided into a narrowly subdivided plurality of regions, wherein each of said narrowly subdivided plurality of regions has a temperature, comprising:
    detector means for detecting an amount of ray radiated respectively from each of said narrowly subdivided plurality of regions on the surface of said sample, said detector means further comprising scanning means for scanning the surface of said sample;
    heater means for keeping said sample under at least two known temperatures and an unknown temperature; and
    arithmetic operation means for obtaining temperature coefficients of respective amounts of rays radiated from said narrowly subdivided plurality of regions from the amount of radiated rays obtained by keeping said sample under said at least two known temperatures, and for obtaining the temperature of respective ones of said narrowly subdivided plurality of regions of said sample at said unknown temperature in accordance with said temperature coefficients and said amount of radiated rays at said unknown temperature.

7. A system for measuring surface temperature distribution in accordance with said claim 6, wherein said radiated ray is an infrared ray and said detector means is an infrared ray detector.

8. A system for measuring surface temperature distribution in accordance with said claim 6, further comprising display means for displaying said amount of radiated rays and the temperature of respective ones of said narrowly subdivided plurality of regions on the surface of said sample.

9. A system for measuring surface temperature distribution in accordance with claim 8, wherein said display means comprises a color display.

10. A system for measuring surface temperature distribution in accordance with said claim 6, wherein said scanning means is capable of mounting said sample and is a movable scanner which can move at least in bidimensional directions.

11. A system for measuring surface temperature distribution in accordance with said claim 10, further comprising display means for displaying said amount of radiated rays and the temperature of respective ones of said narrowly subdivided plurality of regions on the surface of said sample.

12. A system for measuring surface temperature distribution in accordance with claim 11, wherein said display means comprises a color display.

13. A method for measuring surface temperature distribution in accordance with said claim 1, wherein said radiated ray is an infrared ray.

14. A system for measuring a surface temperature distribution of a sample comprising a plurality of coexisting materials having different radiation coefficients of radiated infrared rays at the same temperature and divided into a narrowly subdivided plurality of surface regions, said system comprising:

condition setting means for placing the sample under at least two known temperature conditions and a measuring condition, said setting means comprising a heater for heating the sample;

detector and scanning means for measuring an amount of infrared rays radiated respectively from each of said narrowly subdivided plurality of regions on the surface of the sample at the at least two known temperature conditions and the measuring condition, and converting the measured amount of infrared rays into representative electrical signals;

memory means for storing information corresponding to the representative electrical signals on the amount of infrared rays measured from each of the narrowly subdivided plurality of surface regions under the at least two known temperature condition and the measuring condition obtained by the detector and scanning means;

control means for obtaining the temperatures of the narrowly subdivided plurality of regions on the sample surface at the measuring condition, from the amount of infrared rays measured by said detector and scanning means and the information stored in said memory means, said control means comprising means for calculating the difference in the amount of infrared rays measured by said detector and scanning means at said at least two known temperatures, and means for calculating the temperature of the sample, in accordance with the amount of infrared rays measured by said detector and scanning means at the measuring condition, and the difference in the amount of infrared rays calculated by said calculating means; and display means for displaying the surface temperature distribution comprising the temperature of the respective ones of the narrowly subdivided plurality of surface regions for the sample being measured.

15. The system of claim 14, wherein said detector and scanning means comprises an infrared ray detector for measuring the amount of infrared rays at the surface of the sample, a movable scanner on which the sample is mounted, control means for controlling the infrared ray detector and the movable scanner, a linearizer for making linear the relationship between the temperature and the electrical signals representing the amount of measured infrared rays, and an A/D converter for converting the linearized electrical signal into a digital signal.

16. The system of claim 15, wherein said condition setting means comprises a heater for heating the sample to said at least two known temperatures.

17. The system of claim 14 or 15, wherein said memory means comprises RAM devices and wherein said control means comprises a microprocessor device and a read-only memory device.

18. The system of claim 14 or 15, wherein said display means comprises a display means for displaying colored pictures of the temperature distribution of the measured sample.

19. The system of claim 14, wherein the sample is a small sample and the detector means comprises an infrared ray microscope.

20. The system of claim 14, wherein the sample is a small sample comprising a semiconductor integrated circuit and wherein said detector and scanning means includes an infrared ray microscope for measuring the infrared rays from the surface of the semiconductor integrated circuit.

* * * * *

UNITED STATES PATENT AND TRADEMARK OFFICE
CERTIFICATE OF CORRECTION

PATENT NO. : 4,389,125
DATED : JUNE 21, 1983
INVENTOR(S) : KOBAYASHI ET AL.

It is certified that error appears in the above-identified patent and that said Letters Patent is hereby corrected as shown below:

Front page, after [22] insert the following:

--[30] FOREIGN APPLICATION PRIORITY DATA

October 2, 1979 [JP] Japan ....... 54-127041--.

Col. 2, line 59, delete "$T_o= (T_2-T_1)1(-$";

line 60, before the equation insert

--$T_o=(T_2-T_1)1(-$ --.

Signed and Sealed this

Sixth Day of December 1983

[SEAL]

Attest:

GERALD J. MOSSINGHOFF

Attesting Officer  Commissioner of Patents and Trademarks